United States Patent [19]

Lembeck

[11] Patent Number: 5,121,881
[45] Date of Patent: Jun. 16, 1992

[54] AIR-FRESHENING LIQUID CONTAINER
[75] Inventor: William Lembeck, Forest Hills, N.Y.
[73] Assignee: Reckitt & Colman Inc., Wayne, N.J.
[21] Appl. No.: 637,437
[22] Filed: Jan. 4, 1991
[51] Int. Cl.[5] .............................................. A61L 9/04
[52] U.S. Cl. ........................................ 239/44; 239/34
[58] Field of Search ............... 239/34, 44, 49, 51.5, 239/53-60

[56] References Cited

U.S. PATENT DOCUMENTS

| | | | |
|---|---|---|---|
| 2,241,022 | 5/1941 | Sierad et al. | 239/44 |
| 2,766,066 | 10/1956 | Hopson et al. | 239/44 |
| 3,283,787 | 11/1966 | Davis | 239/34 |
| 4,017,030 | 4/1977 | Coplan et al. | 239/44 |
| 4,913,350 | 4/1990 | Purzycki | 239/44 |

FOREIGN PATENT DOCUMENTS

| | | | |
|---|---|---|---|
| 522993 | 3/1956 | Canada | 239/44 |
| 2042340 | 9/1980 | United Kingdom . | |

Primary Examiner—Andres Kashnikow
Assistant Examiner—Karen B. Merritt
Attorney, Agent, or Firm—Frederick H. Rabin; Charles A. Blank

[57] ABSTRACT

A container for an air freshening liquid including a bottom portion having a bottom wall and at least one lateral wall. The container has a liquid-permeable upper wall. The lateral wall includes at least one open groove extending to the upper wall whereby liquid in the container rises by capillary action to the upper wall which absorbs the liquid for evaporation.

7 Claims, 4 Drawing Sheets

AIR-FRESHENING LIQUID CONTAINER

This invention relates to a container for a liquid and, more particularly, to a container for an air freshening liquid which evaporates into the ambient air.

BACKGROUND OF THE INVENTION

Heretofore, there has been proposed an air freshening liquid container utilizing a silicone rubber film on the outside surface of an evaporator pad to contain liquid in the container and to avoid spills. Silicone rubber is a permeable material which allows the air freshener to escape in vapor form but not in its liquid state. The shortcoming of this previously proposed container is that it operates only in an upside-down position.

One commercial air freshening liquid container utilizes a wick composed of multiple fine synthetic fibers running lengthwise along the wick's axis with the top end of the wick into contact with the bottom surface of an evaporator pad where the transfer of liquid from the wick to the pad is accomplished.

It is an object of the present invention, therefore, to provide a new and improved container for a liquid which avoids one or more of the disadvantages of prior such containers.

It is another object of the invention to provide a new and improved container for an air freshening liquid which does not require a fiber wick.

SUMMARY OF THE INVENTION

In accordance with the invention, a container for a liquid comprises a bottom portion including a bottom wall and at least one lateral wall. The container also includes a liquid-permeable upper wall. The lateral wall includes at least one groove extending to the upper wall, whereby liquid in the container rises by capillary action to the upper wall which absorbs the liquid for evaporation.

For a better understanding of the present invention, together with other and further objects thereof, reference is made to the following description, taken in connection with the accompanying drawings, and its scope will be pointed out in the appended claims.

BRIEF DESCRIPTION OF THE DRAWINGS

Referring now to the drawings.

DESCRIPTION OF THE PREFERRED EMBODIMENT

Figure 1:
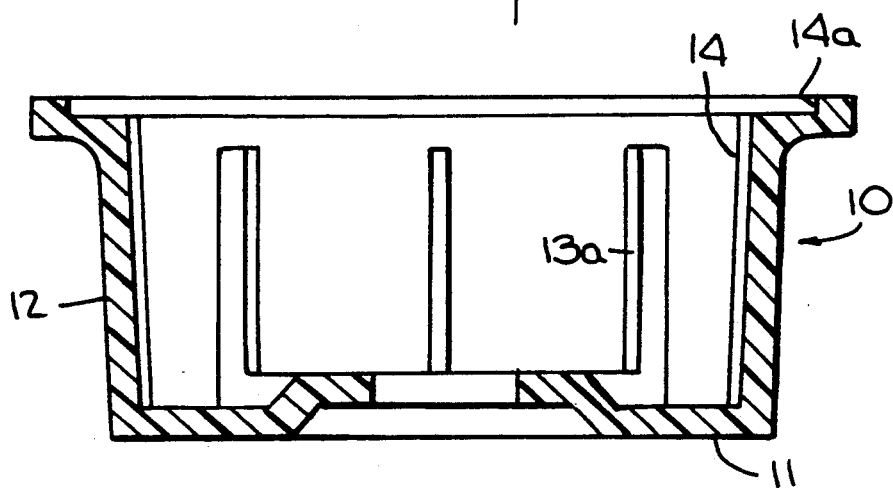
FIG. 1 is a sectional view, in elevation, of a container portion for a liquid constructed in accordance with the invention.
Figure 2:
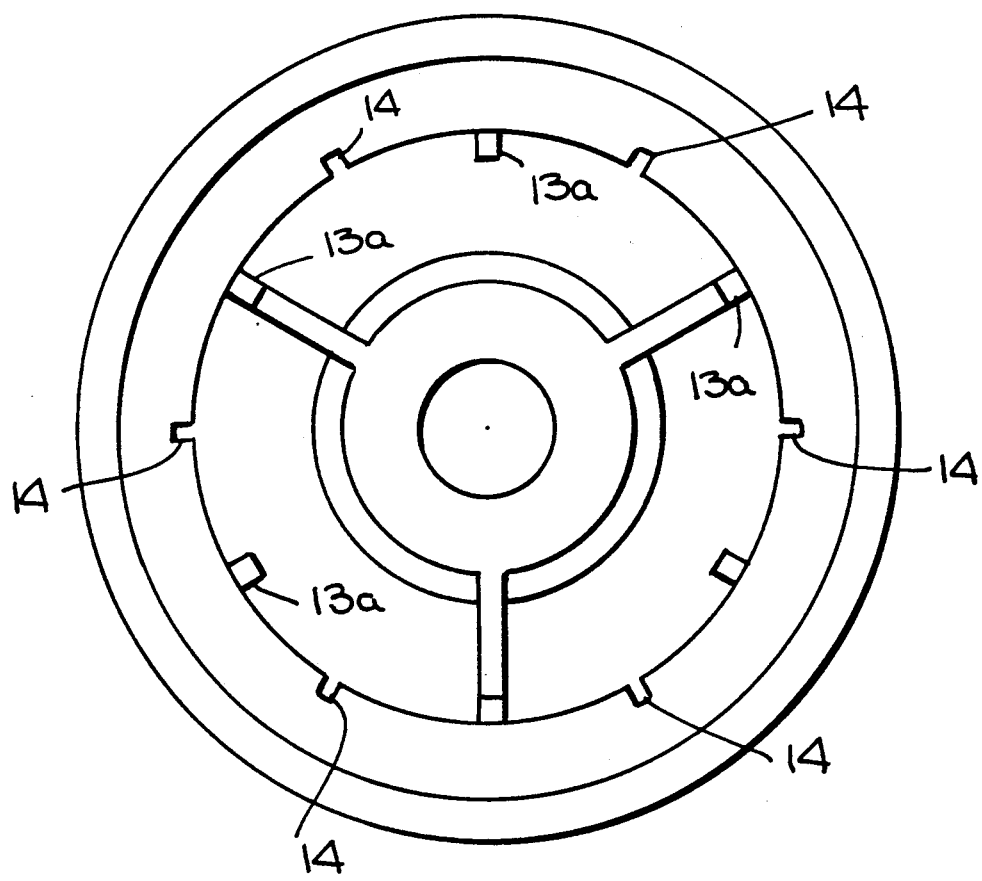
FIG. 2 is a top plan view of the FIG. 1 container portion.
Figure 5:
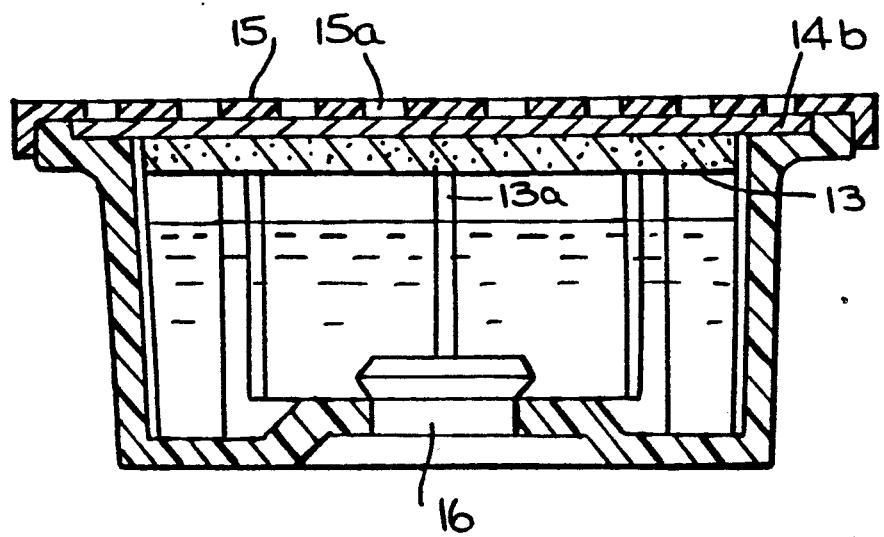
FIG. 5 is a sectional view, in elevation, of a container with a top portion thereon.

Referring now more particularly to the drawings, FIG. 1 represents a container for a liquid, preferably an air freshening liquid, comprising a bottom portion 10 including a bottom wall 11 and at least one lateral wall 12. The container includes a liquid-permeable upper wall which is not shown in FIG. 1 but which appears as evaporator pad 13 in the exploded view of FIG. 3. The evaporator pad is supported by ribs 13a of the lateral wall 12. The lateral wall 12 includes at least one groove 14 which is apparent in FIGS. 1, 2 and 3 extending to the upper wall formed by the evaporator pad 13, whereby liquid in the container rises by capillary action to the upper wall which absorbs the liquid for evaporation. Thus the bottom portion 10 is an upright cylinder having an open top end. The upper wall 13 is paper, with a cotton blend. The paper is covered by a gas-permeable chemically treated paper 14b shown in FIG. 3 and FIG. 5 seated in the groove 14a of FIG. 3. A top portion 15 having pores 15a for the escape of gas is snapped onto the bottom portion of the container. The top portion 15 may have any desired shape, for example, an inverted bowl shape with pores.

Figure 3:
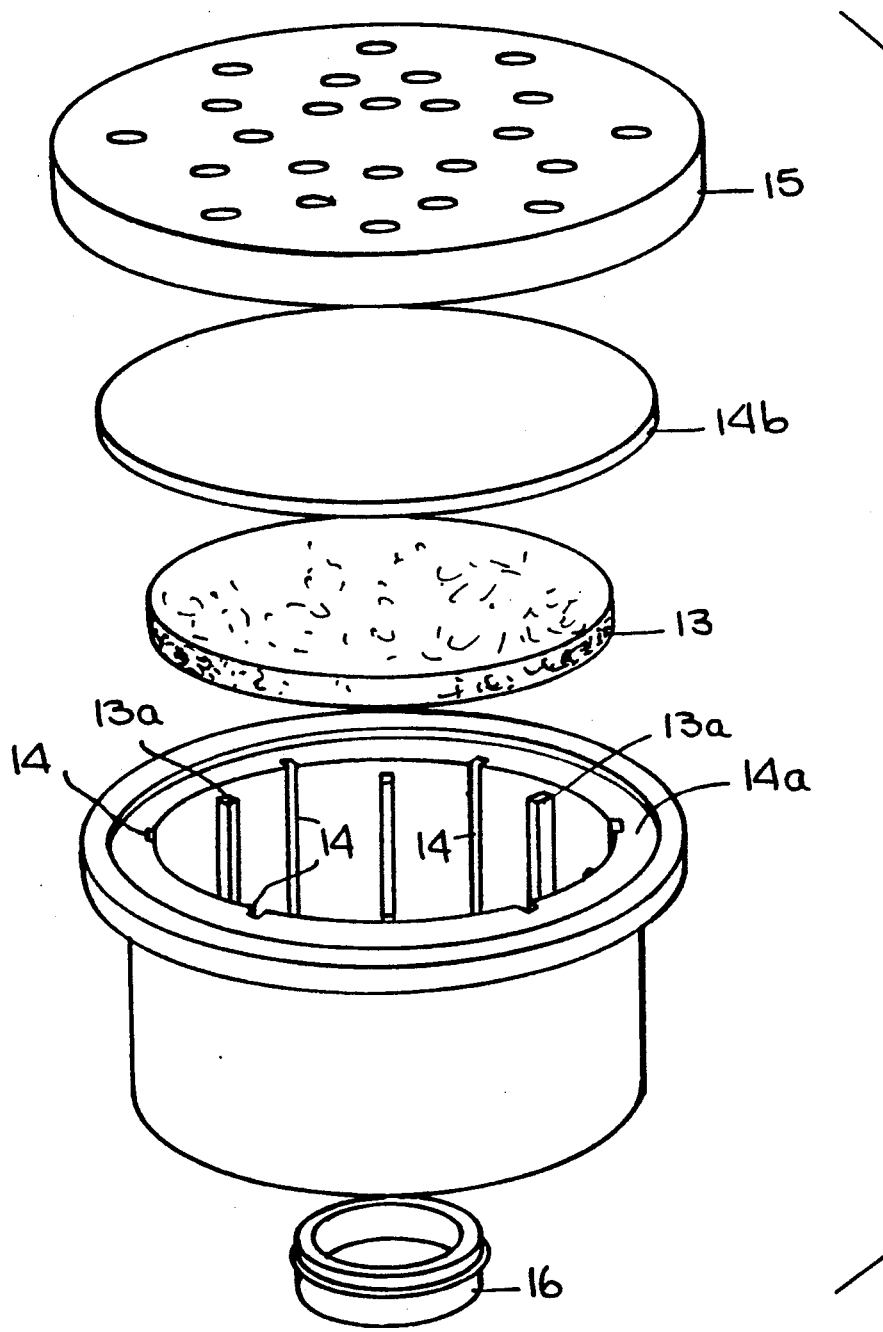
FIG. 3 is an exploded view of a container constructed in accordance with the invention.
Figure 4:
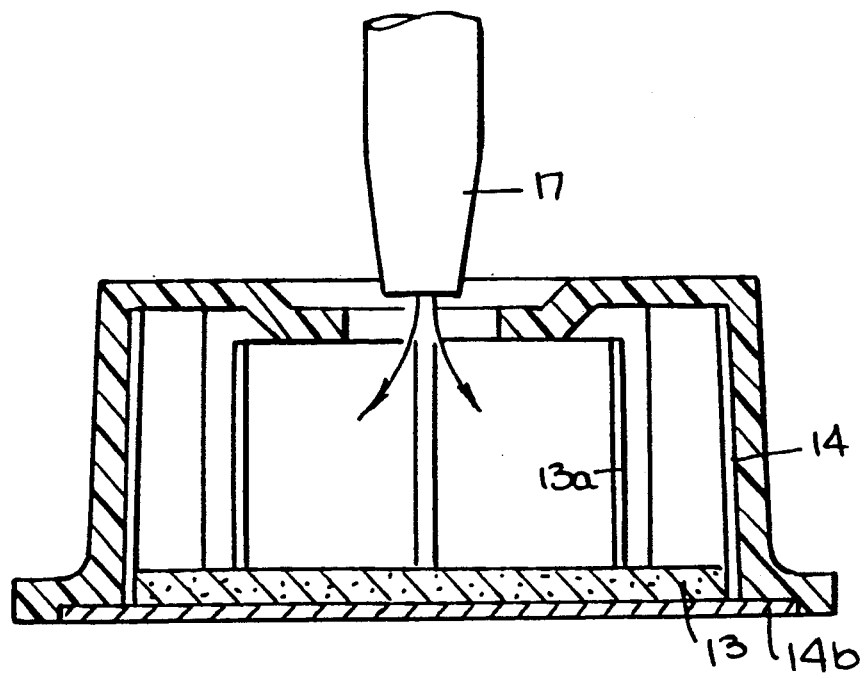
FIG. 4 is a sectional view, in elevation, representing a container portion upside down.

As represented in FIG. 4, the container preferably is filled with air freshening liquid in an upside down condition with a bottom plug 16 of FIG. 3 removed so that a suitable nozzle 17 may be utilized to insert the liquid.

A short explanation of capillary pressure would be helpful in understanding the concept of open-channel wicking.

Figure 6:
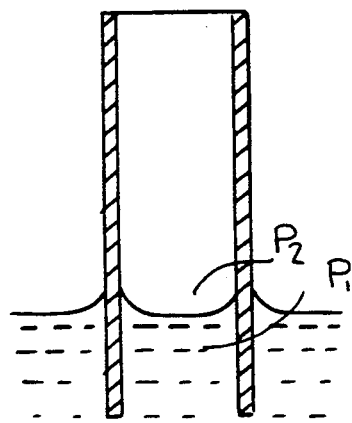
FIG. 6 is a diagram of a capillary tube in a liquid to aid in understanding the invention.

Capillary pressure is defined as the difference in pressure between that just below the surface of a liquid and that just above the surface of the liquid, as shown in FIG. 6. It can be expressed as $$P_c = (P_v - P_l) \tag{1}$$

where $P_v$ is the vapor pressure and $P_l$ is the liquid pressure.

Figure 7:
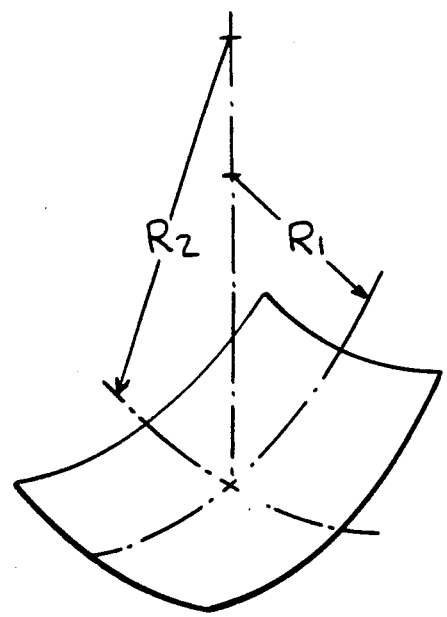
FIG. 7 is a diagram representing the curvature of a meniscus to aid in understanding the invention.

When a meniscus (curved surface) is formed at the liquid-vapor interface, as shown in FIG. 7, the capillary pressure can be calculated by the equation developed by Laplace and Young in the late 1700's.

$$P_c = s(1/R_1 + 1/R_2) \tag{2}$$

in which $R_1$ and $R_2$ are the principal radii of curvature of the meniscus and s is the surface tension coefficient of the liquid.

To find the value of $(1/R_1 + 1/R_2)$ for wick pores of simple geometry, the values of this expression can often be determined theoretically.

For example, $R_1$ is equal to $R_2$ for a cylindrical pore or tube and the value of R can be determined by the equation $$R = r/\cos A \tag{3}$$

Figure 8:
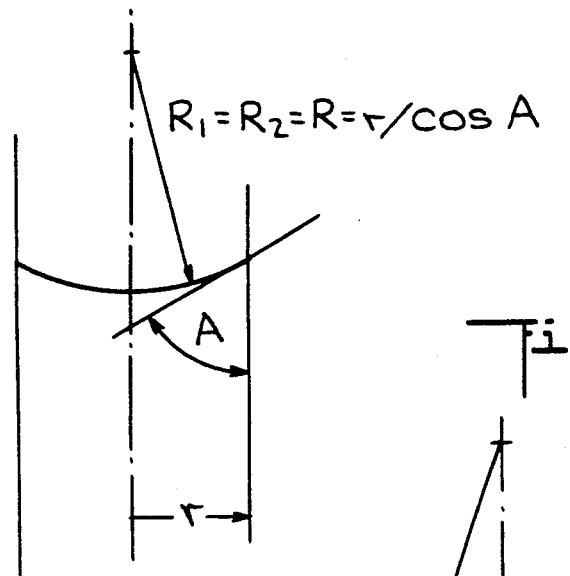
FIG. 8 is a diagram representing a meniscus in a cylindrical pore to aid in understanding the invention.

From FIG. 8 this relationship appears quite easily. Here, r is the radius of the cylindrical tube and A is the wetting angle.

FIG. 8 represents the meniscus in a cylindrical pore.

Substitution of R from Equation (3) into Equation (2) gives the value of the capillary pressure for the cylindrical tube.

$$P_c = s/(\cos A/r + \cos A/r) = 2s \cos A/r \quad (4)$$

It can be seen in this equation that the maximum capillary pressure exists when the cosine of the wetting angle is unity, i.e., A equal to zero. This can often be accomplished by adding specific chemical surfactants to the liquid.

A similar formula can be derived for a pore consisting of an open-channel rectangular groove. There is no meniscus in the open side of the groove; therefore, the radius of curvature is infinity. The other radius of curvature is equal to half the groove width divided by cos A (as long as the groove depth is at least half the groove width). The equation for capillary pressure is:

$$p_c = s(\cos A/r + \cos A/\infty) = s(2 \cos A/w + 0)$$

$$P_c = 2s \cos A/w \text{ where w is the groove width} \quad (5)$$

Figure 9:
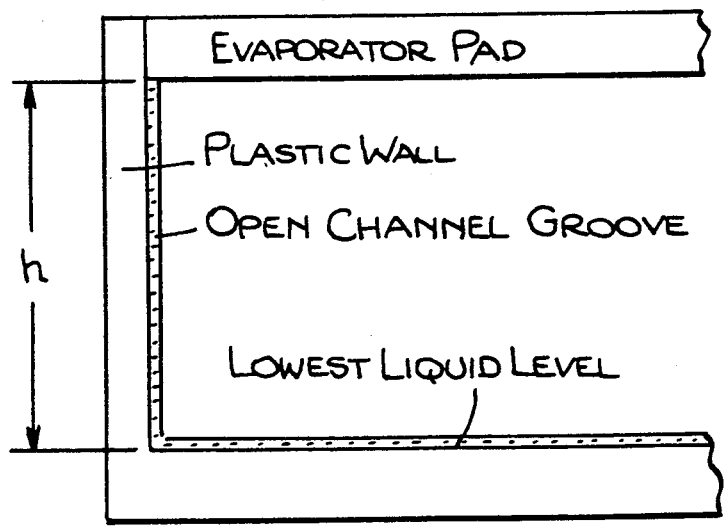
FIG. 9 is a diagram representing head pressure vs. capillary pressure to aid in explaining the invention.

This open-channel rectangular wicking pore is particularly valuable, because it can be molded directly into the plastic container holding the liquid air freshener. As shown in FIG. 9, in order to pump liquid to the evaporator pad from the lowest level of the liquid, the capillary pressure, $P_c$, must be greater than the liquid head pressure, $P_h$.

FIG. 9 represents Head Pressure vs. Capillary Pressure.

The head pressure is defined as the weight density of the liquid times the gravitational constant and the head:

$$P_h = D \times g \times h \quad (6)$$

where $P_h$ = head pressure in dynes/cm$^3$
D = weight density in gms/cm$^3$
g = gravitational acceleration in cm/sec$^2$
h = head in cm From equation (5) $P_c = 2s \cos A/w$. Therefore, in order to be able to pump liquid from its lowest level in a container to the bottom surface of the evaporator pad, Capillary Pressure must be greater than Head Pressure or, putting it in mathematical terms, $$P_c > P_h \quad (7)$$

and substituting (5) and (6) in equation (7), $$2s \cos A/w > Dgh \quad (8)$$

To find the width of the groove necessary to pump liquid up the side walls of a container, one could use equation (8) with rearranged terms:

$$w < 2s \cos A/Dgh \quad (9)$$

Looking at all the terms on the right side of the equation, there are four variables that must be known before a value for the groove width, w, can be obtained.

I performed several experiments to determine the approximate values of these variables. Within rather broad limits these values could be assumed to be:

s cos A = 25 dynes/cm
D = 0.9 gms/cm$^3$
g = 980 cm/sec$^2$
h = 2 cm container

Substituting these values into equation (9) gives a maximum value for the width of the groove:

w < 2(25)/(0.9)(980)(2)

w < 0.028 cm or 0.011 in.

From the foregoing theoretical discussion and the results of many experiments, I have determined that it is quite possible to pump a liquid out of a container simply by using a groove molded into the wall of the container. Furthermore, experiments have shown that the depth of the groove need be no greater than the width of the groove to provide sufficient flow to keep the underside of the evaporator pad wet and conducive to continuous flow. Theoretically only one groove is needed to provide the necessary quantity of air freshener for adequate delivery. However, it is felt that a series of grooves, perhaps eight, would always provide sustained delivery of the air freshener to the ambient surroundings. I have found that the cosine of the wetting angle A is almost always in the range of from 0.8 to 1 for any material using water or alcohol as its base. Accordingly, a wide range of materials may be used for the air-freshening liquid. While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

I claim:

1. A container for a liquid comprising:
   a bottom portion including a bottom wall and at least one lateral wall;
   a liquid-permeable upper wall;
   said lateral wall including at least one open groove extending to said upper wall, whereby liquid in said container rises by capillary action to said upper wall which absorbs the liquid for evaporation.

2. A container in accordance with claim 1 in which said liquid is an air-freshening liquid.

3. A container in accordance with claim 1 in which said bottom portion is an upright cylinder having an open top end.

4. A container in accordance with claim 1 in which said upper wall is paper, with a cotton blend.

5. A container in accordance with claim 1 in which said paper is covered by a gas-permeable chemically treated paper adherent to said container.

6. A container in accordance with claim 1 in which said lateral wall includes a plurality of open grooves extending to said upper wall.

7. A container in accordance with claim 1 in which said lateral wall includes a plurality of ribs extending to and supporting said upper wall.

* * * * *